(12) United States Patent  
Waram et al.

(10) Patent No.: US 6,533,752 B1  
(45) Date of Patent: Mar. 18, 2003

(54) VARIABLE SHAPE GUIDE APPARATUS

(76) Inventors: Thomas C Waram, 1063 King St. West, Suite 204, Hamilton, ON (CA), L8S 1L8; John D. Unsworth, 365 Lodor St., Ancaster, ON (CA), L9G 2Z5

( * ) Notice: Subject to any disclaimer, the term of this patent is extended or adjusted under 35 U.S.C. 154(b) by 0 days.

(21) Appl. No.: 09/477,640

(22) Filed: Jan. 5, 2000

(51) Int. Cl.[7] .................. A61M 31/00; A61M 37/00
(52) U.S. Cl. ............... 604/95.05; 604/530; 604/531
(58) Field of Search .................. 604/530, 531

(56) References Cited

U.S. PATENT DOCUMENTS

| | | |
|---|---|---|
| 5,334,168 A | 8/1994 | Hemmer |
| 5,389,073 A * | 2/1995 | Imran .................. 600/435 |
| 5,395,332 A | 3/1995 | Rossemann et al. |
| 5,454,794 A | 10/1995 | Narciso, Jr. |
| 5,462,527 A | 10/1995 | Stevens-Wright |
| 5,472,418 A | 12/1995 | Palestrant |
| 5,476,100 A | 12/1995 | Galel |
| 5,478,330 A | 12/1995 | Imdan |
| 5,484,070 A | 1/1996 | Osypka |
| 5,484,412 A | 1/1996 | Pierpont |
| 5,507,725 A | 4/1996 | Savage |
| 5,531,685 A | 7/1996 | Hemmer |
| 5,531,687 A | 7/1996 | Snoke |
| 5,531,689 A | 7/1996 | Burns et al. |
| 5,545,200 A | 8/1996 | West |
| 5,545,209 A | 8/1996 | Roberts |
| 5,558,643 A | 9/1996 | Samson |
| 5,562,619 A | 10/1996 | Mirarchi |
| 5,569,201 A | 10/1996 | Burns |
| 5,571,087 A | 11/1996 | Rossemann et al. |
| 5,571,685 A | 11/1996 | Accisano, III |
| 5,846,247 A | 12/1998 | Unsworth |

FOREIGN PATENT DOCUMENTS

EP          279316 A          9/1988

* cited by examiner

*Primary Examiner*—Brian L. Casler  
*Assistant Examiner*—Jeremy Thissell

(57) ABSTRACT

The apparatus includes a flexible, elongated tubular member and is comprised of a tube of superlastic metal which in response to changing temperatures resists to a greater or less degree the bending moment imposed by a biasing element, thereby altering the shape of the tubular member as a function of temperature and producing a broad range of shapes.

13 Claims, 2 Drawing Sheets

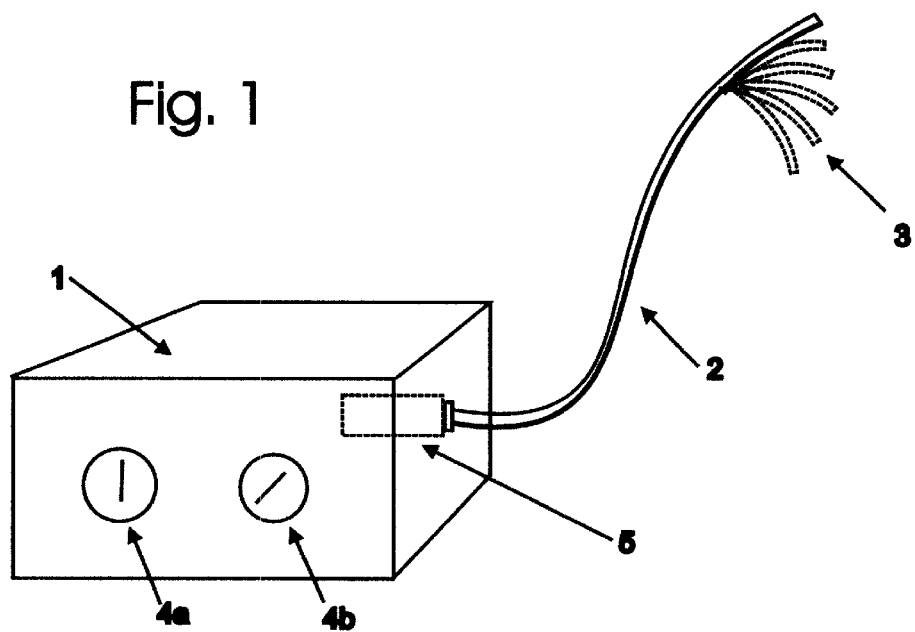
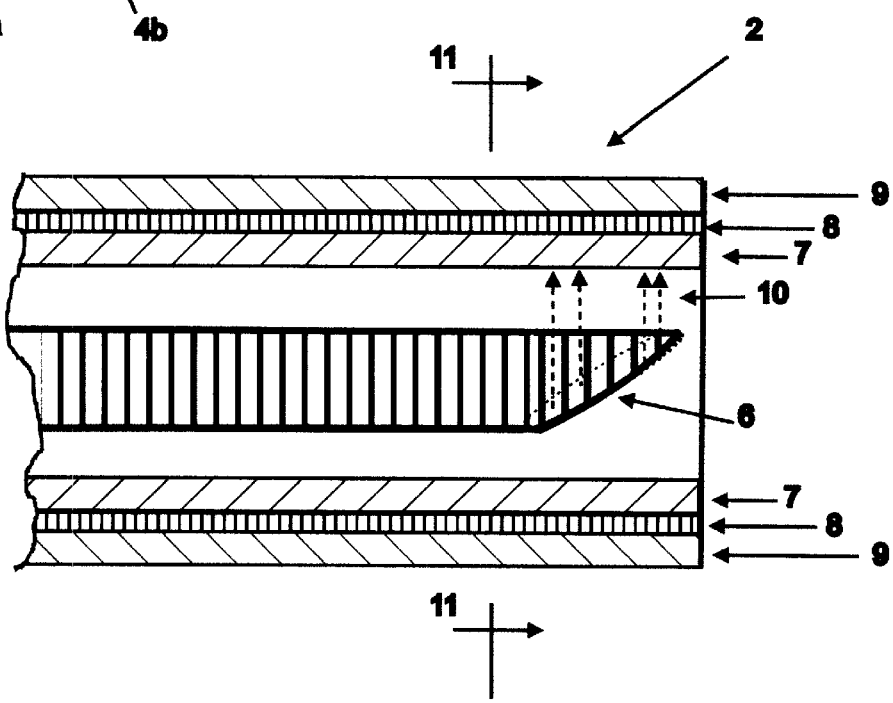
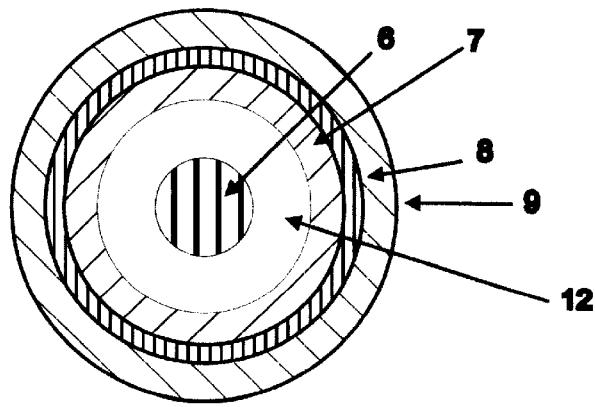

VARIABLE SHAPE GUIDE APPARATUS

FIELD OF THE INVENTION

The field of the invention is steerable catheters, cannulae, guides and the like, that are designed to be steered through body cavities and aimable at obstructions, organs, or tissues within the body from a position external from the body.

BACKGROUND AND SUMMARY OF THE INVENTION

A great deal of research has been directed at developing a catheter or guide having a distal end which, when inserted into a body, is readily steerable and aimable to advance the device through the body cavities and passageways. It has been observed that materials exhibiting mechanical memory properties triggered by heat are particularly useful for enhancing the maneuverability of catheters of like devices. The materials are commonly called "temperature-activated memory materials" or "shape memory alloys" or simply "SMA", because they move to assume a predetermined shape when heated to a predetermined temperature. Nitinol, a nickel-titanium alloy, is one such SMA that has been formed into memory element strips and deployed in the distal end of a catheter. Heating the nitinol memory element strips to a given temperature using an electric current provided by a power supply causes the memory elements to deform to assume a predetermined shape, thereby deflecting the distal end of the catheter. See, for example, U.S. Pat. Nos. 4,543,090; 4,601,705; and 4,758,222 for descriptions of known memory element systems for steering and aiming catheters, cannulae, and the like.

The shape that is recovered by heating is first imparted into the device at high temperature during the manufacturing process. When the device is cooled below its martensitic start temperature, it can be distorted into another arbitrary shape. When however the device is heated above its austenitic start temperature, the imparted shape is partly recovered and when it is further heated to its austenitic finish temperature, the shape is fully recovered. These devices utilize these characteristic to change the shape of the distal tip of the devices by heating the distal tip of the device while it is in its martensitic phase. When it transformed into its austenitic phase, the shape is recovered, and the changed shape can be used to redirect the device.

Use of shape memory nitinol previously has been used in "strip" or "rod" form in the construction of steerable and aimable apparatus. Such nitinol strips and rods are solid core elements having a circular, rectangular, or other similar cross-sectional shape. In use, these solid core memory elements strips or rods are placed on opposing sides of a central lumen formed in an apparatus about the circumference of the apparatus. Selective activation of these memory element strips or rods results in articulation of the apparatus. See, for example U.S. Pat. No. 4,601,705 for a disclosure of a four-memory element strip steering and aiming system and U.S. Pat. No. 4,758,222 for a disclosure of a steering and aiming system using a spring and one temperature activated memory element strip. Similarly, U.S. Pat. No. 5,334,168 describes a variable shape guide apparatus that is constructed from a tube of SMA that is heated in its martensitic form to recover an imparted shape as it transforms into austenite at a higher temperature. This recovered shape then allows the device to be redirected down the body lumen. The preferred embodiments that utilize the shape memory effect from martensite to austenite do not disclose a biasing element and make clear that the shape change is effected by the transition from the martensitic phase to the austenitic phase. The only preferred embodiment of U.S. Pat. No. 5,334,168 4 that includes superlastic nitinol (which is in the austenitic phase) is expressly not heated to effect a shape change but rather uses a guide wire to do so:

"In this embodiment, nickel titanium tube 122 is made, for example, of superelastic nitinol. It will be understood that control means is not needed to heat superelastic nitinol since it is already in an activated (above transition) temperature. For example, a superelastic nitinol tube 122 is formed in a present curved shape and a guide wire (not shown) is used to return the nitinol tube 122 to a straight shape."[Column 4, line 57 to 64]

In all previous steerable SMA systems the steering means is achieved by heating the SMA while it is in its martensitic form and recovering a different shape as it transforms into its austenitic form. The difficulty with utilizing the transformation from martensite to austenite, or visa versa, to effect shape change and thereby allow for steering is two-fold: firstly the device in its matensitic state is not as springy as in its austenitic state, which makes it more difficult for the operator to manipulate the device from outside the body; secondly, it is difficult to partly transform the SMA to allow for a partial change in shape of the steerable portion of the device. The second shortcoming is due to the fact that shape recovery occurs over the relatively small temperature range from the austenitic start temperature ($A_s$) to the austenitic finish temperature ($A_f$).

What is needed is a system that allows for steering but at the same time maintains the springy qualities of SMA in its austenitic phase. What is also needed is a system that allows for partial changes in the shape of the steerable portion of the device to permit a greater range of steerability.

The invention herein disclosed is a steerable device that effects shape change entirely while above the austenitic finish temperature and does not rely on recovering the imparted shape at the transition between austenite and martensite. This invention herein disclosed relies on the fact that a tube of SMA in its austenitic form becomes stiffer as the temperature of the material is increased. This increase in stiffness or modulus is approximately linear as a function of increased temperature and therefore allows for a gradual increase in stiffness in response to increases in heat energy applied to the device. For example, if an appropriate force is applied normal to the longitudinal axis of a tube (a bending force) and the tube is made of SMA material that remains in the austenitic phase, when the tube is heated, the tube will become stiffer, partly overcoming the bending force and thereby changing its shape or radius of curvature. This shape change can be used to steer the device. Depending upon the shape of the tube along its longitudinal axis in its unloaded mode and the nature of the impending biasing forces, the tube can be designed to assume many different shapes as it is heated and cooled. The unloaded shape of the SMA tube and the shape of the biasing element can be simple or complex. For example the unloaded SMA tube could be helical, and the biasing element could be contoured to exert the appropriate forces to hold the unit in a straight configuration; upon heating the unloaded helical shape of the SMA tube could come to dominate the shape of the unit.

In summary, the shape change is not due to recovering a shape by heating the SMA between the $A_s$ and the $A_f$ temperature; it is instead a result of the stiffening of the SMA that occurs solely above the $A_f$ while it is in the austenitic phase. It should be noted that this shape change is dependent upon first, a biasing force distorting the SMA device from its unloaded shape (that being the shape it would have at or above the $A_f$ temperature if no biasing force was applied), and second the application of heat to the device causing it to overcome the biasing force somewhat; and moving the device from its distorted shape closer to unloaded shape. The stiffening of austenite due to heating has been described by Unsworth and Waram in U.S. Pat. No. 5,904,657 to stiffen guides wires but without a biasing force that allows it to steered.

In the case of such a device being introduced into the bloodstream, the heat applied to the tube would for example be above the temperature of the blood and as more heat is applied to the tube it would become stiffer and with the said appropriate biasing force, the tube would change its shape; but when the heat is removed or reduced, the blood would cool the tube and the tube would become less rigid and more subject to the appropriate biasing force which would tend to return the tube to the same shape it assumed prior to the heat being applied. It can be appreciated that this change of shape can be used for the purpose of steering the distal end of the device; but also this change of shape could occur in a repetitive fashion which would cause the tube to pulse or wriggle. Both of these effects can be utilized to assist in advancing the device along the lumen of the body into which it is introduced. This pulsing or wriggling would reduce the static and dynamic friction at the interface between the device an the wall of the lumen as it is being advanced into the lumen of the vessel.

The use of electricity to heat the said tube has been suggested in a number of patents, including U.S. Pat. No. 5,334,168 referred to above. While one of the preferred embodiments of the invention would include such a heating means, a more convenient method is that described in U.S. Pat. No. 5,846,247 by Unsworth and Waram which patent is incorporated herein by specific reference. That patent describes how photo-thermal heat produced by a laser is introduced into the lumen of the tube by means of an optical fiber. The said optical fiber directing the photo-thermal energy onto the inside walls of the lumen of the tube by means well known to the art. The heating of the tube can then be controlled in exquisite precision by varying the output of the laser and also perhaps by moving the optical fiber back and forth inside the tube to change the location where the photo-thermal energy is delivered to the said tube. By appropriately changing the part of the tube that is heated, the austenitic tube with appropriate biasing, as described above, could be caused to pulsate or wriggle in addition to pointing in another direction. While reference is made to the methods described in said Unsworth and Waram U.S. Pat. No. 5,846,247, it is to be understood that the preferred embodiments of the invention include any means of heating the tube to cause it to change shape with the appropriate biasing force.

A preferred embodiment of the invention includes a biasing tube, coil or other element that partly or completely surrounds the SMA tube. The SMA tube, in its unloaded state would be principally austenitic at body temperature and would become stiffer with the application of heat. This biasing tube or element would typically be made of stainless steel, but could be made of plastic or other suitable materials. This tube or element would be typically bent by the surgeon into a curved shape that he might think appropriate to initiate turns for advancing the guide into the lumen of a body vessel. This bending of the distal end of the guide by the surgeon provides the biasing force that distorts the unloaded shape of the SMA tube. The stainless steel tube or coil although somewhat springy, is bent beyond its yield strength by the surgeon to impart the appropriate curve. However, the superlastic SMA tube being very flexible does not suffer the same plastic deformation due to the said bending. The superlastic tube bends either by elastic deformation of austenite or by the formation of stress-induced martensite from the austenite, in response to the force of the new shape that has been imparted on the biasing element. It is this biasing force that the heating of the SMA tube overcomes to change the shape from the curved shape to a straighter shape in the example above, where the SMA tube was straight in its unloaded shape. It should be noted that the shape of the biasing element or tube need not be set by the surgeon, but could be set by the manufacturer. Also, the biasing tube or element could be made up of more than one element.

The preferred embodiment of this invention includes an optical fiber that projects photo-thermal energy onto the inside walls of the SMA tube thereby heating the said tube. The termination of the optical fibre can include projection means that are well known to the art and includes the simple projection from the end of the optical fiber, with attendant beam divergence, to side firing means that includes what is referred to in the art as leaky fibers. Leaky fibers are optical fibers that permit the photo-thermal energy to project out the side of the fiber over a determined length. Termination means also includes mirroring of the distal end of the optical fibre to redirect the photo-thermal energy onto the walls of the SMA tube.

As described in U.S. Pat. No. 5,846,247 by Unsworth an Warm which patent is incorporated herein by specific reference, the projection of the photo-thermal energy can be modulated while being directed at specific points or along defined tracks as the optical fiber is moved along the inside of the SMA tube being heated. It can be readily seen that a preferred embodiment of this invention might include an optical fiber that moves back and forth inside the SMA tube heating and thereby stiffening only parts of the SMA tube. This selected heating and stiffening would when combined with the forces imparted by the biasing element could result in many desired shapes. The movement of the fiber could be computer controlled and motor driven by means well known to the art. A simpler preferred embodiment of the invention would be comprised of a stationary optical fibre.

Additional features and advantages of the invention will become apparent to those skilled in the art upon consideration of the following detailed description of the preferred embodiments exemplifying the best mode of carrying out the invention as presently perceived.

BRIEF DESCRIPTION OF THE DRAWINGS

The detailed description particularly refers to the accompanying figures in which:

FIG. 1 is a perspective view of a steerable and aimable apparatus embodying the present invention showing the control box 1 that contains a laser 5 and thermal control 4a and pulsing control 4b as well as the guide 2 changing shape at the distal end 3.

FIG. 2 is an enlarged view of one portion of the distal end of one embodiment of the apparatus in FIG. 1 showing a single SMA tube 7 encased in an thermal insulating barrier 8 both of which are encased in a biasing tube 9. An optical fiber 6 is shown delivering photo-thermal energy 10 to the inside wall of the lumen of the SMA tubing 7.

FIG. 3 is a transverse sectional view taken along line 11—11 of FIG. 2. showing the guide 2 with details as noted in FIG. 2.

DETAILED DESCRIPTION OF THE DRAWINGS

Figure 4:
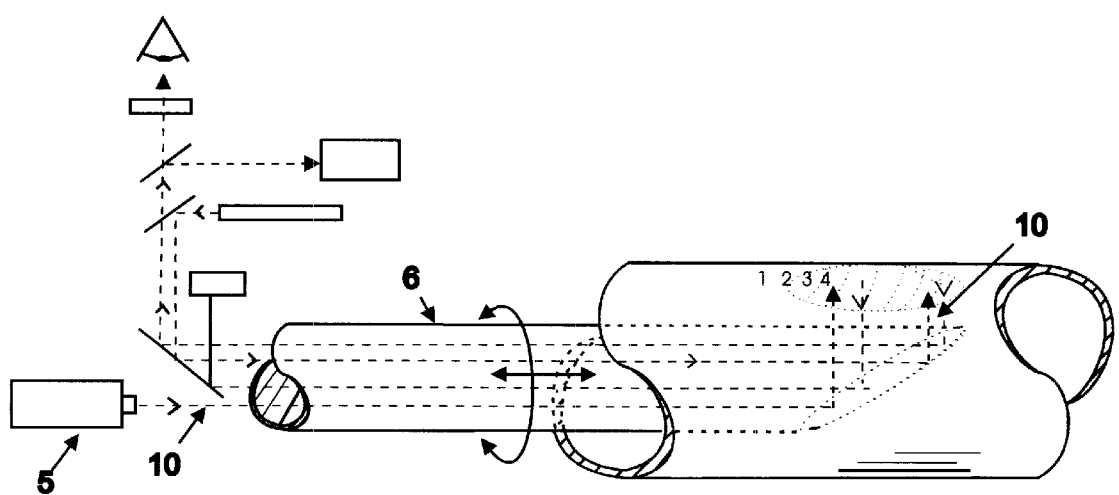
FIG. 4 is a perspective view of a device used in combination with a method taught by Unsworth and Waram in U.S. Pat. No. 5,846,247 for applying thermal energy to the inside of SMA tubes and for heating specific parts of the tubes.

An apparatus embodying the present invention and comprised of a control box 1 is shown generally in FIG. 1 with a detachablely attached tube 2, the distal end of which can articulate at 3. The control box contains a laser 5 that delivers photo-thermal energy to an optical fiber which in turn delivers it to the distal end of the tube 2. The control box 1 also contains means of controlling the amount of photo-thermal energy 4a delivered by the laser to the optical fiber and the pulsing 4b, if any, of the photo-thermal energy delivered to the said optical fiber. Other controls could be included such as a foot-switch or means of controlling various aspects of the photo-thermal energy such as its frequency.

Illustratively, tubular member 2 is formed as shown in FIGS. 2 and 3 to include and optical fiber 6 which can be stationary as shown in FIG. 1, 2, and 3 or can slide back and forth along the longitudinal axis of the tubular member 2 to deliver photo-thermal energy 10 to different parts of the inside wall of the SMA tube 7 as more particularly described in U.S. Pat. No. 5,846,247 and illustrated in FIG. 4. While FIG. 2 shows the photo-thermal energy 10 being directed to only the upper portion of the tube, the distal end of optical fiber 6 could also project the photo-thermal energy to all sides of the inside of the tube using a leaky fiber tip, well known to the art, or by simply allowing the photo-thermal energy to project out a cut end of the distal tip of the optical fibre 7 and relying on the divergence of the beam to project the photo-thermal energy onto the inside walls of the lumen of the SMA tube 7. As referred to above the heating of the SMA tube 7 by the photo-thermal energy causes the tube which is in its austenitic phase to stiffen and act against the biasing force that has been imparted to the biasing tube 9. The SMA tube 7 could be separated from the biasing tube 9 by an insulating material 8. This insulating material 8 would prevent excess heat from being transferred to the body into which the tubular member 2 in inserted. The insulating material could also be added to outside layer of the tubular member 2 if required with the inner layer of insulating material either present or absent. The biasing tube 9 could be a tube as shown in FIG. 2 and 3 or could be a coil, mesh, tape or strip or other suitable biasing element. The biasing tube as noted above must impose a bending moment on the SMA tube 7 so that the SMA tube 7 when heated can stiffen and partly overcome or work against the said bending moment and thereby change the shape of the distal end of the tube 2 and permit the steering or aiming of the distal end of tube 2. The biasing tube or element 9 will thus principally impose a shape to the distal end of tube 2 when the SMA tube is not being actively heated by the application of photo-thermal energy 10. This will cause the springy and relatively flexible SMA tube 7 to bend from its unloaded shape closer to that of the biasing element. As photo-thermal energy is applied to the inside of the SMA tube 7 it will stiffen and overcome the force applied by the biasing tube, changing the shape closer to that of the SMA tube 7 when in its unloaded austenitic shape. Naturally the biasing tube 9 must exert just the right range of forces to allow the SMA tube 7 to move the biasing tube when heated, but to be overcome by the biasing element when cooled. As the SMA tube 7 gets stiffer:as a function of the amount of heating, the distal tip of tube 2 can take a range of shapes. Conversely when the photo-thermal heating is reduced or turned off, approximately the reverse sequence of shapes are produced.

As noted above the heating can also be pulsed and moved to create a vibrating or wriggling distal tip which may be of use for certain purposes. The biasing tube can have a preset shape or can be shaped by the surgeon to a shape that best suits his purpose.

While the preferred embodiment includes the use of nickel-titanium in the tube 7 other materials that exhibit changes in modulus in response to change in temperatures, such as shape memory plastics, could also be used without departing from the scope of the invention.

While the preferred embodiment indicates tubes in a particular order it should be noted that the tubes can be in any order that is convenient for the particular use to which the device is employed. It should also be noted that preferred embodiments of the invention may contain elements that are not tubes, for example the biasing element or the insulating layers may be tapes, meshes, strips or other elements that are not formed into a tubes but serve the same or similar purposes.

While the preferred embodiment utilizes photo-thermal heating, other means of heating the SMA tube could also be used including electricity and chemical reactions.

While the preferred embodiment illustrates an apparatus with a steerable or aimable tip comprised of a SMA tube 7 and biasing tube 9 and insulating tube or layer 8, it should be noted that one of the preferred embodiment includes these elements only in the part of the tubular member 2 that is steerable or aimable, that is in the distal end of the said tubular member. The part of the tubular member proximal to the part that is steerable or aimable need not be composed of these elements and may be comprised of plastic tube or metal tubes, these tubes being connected by the usual means to the said elements that make up the steerable or aimable distal portion.

It should also be noted that preferred embodiments of the present invention may include coatings to increase the lubricity or bio-compatibility of the apparatus.

While the preferred embodiment describes a system having one optical fiber and one lumen, preferred embodiment could have many optical fibers and one or more lumens, movement in various directions could thus be achieved. While the preferred embodiment describes a guide, it is to be understood that the apparatus could be used as a catheter to deliver drugs or other devices to body lumens or for any other purpose where a steerable or aimable While the present invention has been described in conjunction with preferred embodiments, it is to be understood that modifications and variations may be resorted to without departing from the spirit and scope of the invention as those skilled in the art will readily understand. Such modifications and variations are considered to be within the purview and scope of the inventions and appended claims.

What is claimed is:

1. An apparatus for insertion in a preheat body lumen, said apparatus having a steerable distal end portion comprising:
   a first tubular member comprised of a shape memory alloy which adopts a memorized shape in an unloaded austenitic state, said shape memory alloy having an austenite finish temperature below a temperature inside said body lumen, said first tubular member being hollow and having a lumen extending therethrough;
   a second tubular member surrounding said first tubular member and applying a bending moment thereto so as to cause said first tubular member to be deformed from its memorized shape;

heating means for selectively heating at least a portion of said first tubular member to a temperature above said temperature inside said body lumen;

wherein heating said first tubular member causes it to increase in stiffness and resist the bending moment of the second tubular member so as to cause the shape of the distal end portion to tend toward the memorized shape of the first tubular member, and subsequent discontinuation of heating causing the first tubular member to decrease in stiffness, resulting in increased deformation thereof and causing the shape of the distal end portion to tend away from the memorized shape of the first tubular member.

2. The apparatus of claim 1, wherein the steerable distal end portion further comprises a layer of insulating material provided between the first tubular member and the second tubular member or element.

3. The apparatus of claim 1, wherein the steerable distal end portion further comprises a layer of insulating material provided on an outer surface of the second tubular member or element.

4. The apparatus of claim 1, further comprising heating control means to control the intensity and duration of heat applied to the first tubular member by the heating means.

5. The apparatus of claim 4, wherein the heating control means causes intermittent operation of the heating means such that heat is applied to the first tubular member in short pulses separated by periods in which the first tubular member is allowed to cool, resulting in continuous, repetitive movement in the distal end portion.

6. The apparatus of claim 4, wherein the heating control means further controls the location of the heating means within the first tubular member.

7. The apparatus of claim 6, wherein the heating control means simultaneously varies two or more of the intensity, duration and location of the heat applied to the first tubular member by the heating means.

8. The apparatus of claim 1, wherein the heating means comprises an optical fiber received inside the lumen of the first tubular member and which emits photo-thermal energy to heat the first tubular member.

9. The apparatus of claim 8, wherein the optical fiber is slidably received inside the lumen of the first tubular member.

10. The apparatus of claim 9, wherein the photo-thermal energy is emitted from a distal end of the optical fiber, the distal end having a leaky fiber tip or a tip which is terminated so as to project the photo-thermal energy on an inner wall of the first tubular member.

11. The apparatus of claim 1, wherein the second tubular member is comprised of stainless steel.

12. The apparatus of claim 1, wherein the steerable distal end portion of the apparatus has a diameter which allows it to be guided through blood vessels of a human patient.

13. The apparatus of claim 1, wherein the shape memory alloy comprising the first tubular member is a nickel-titanium alloy.

* * * * *